United States Patent
Ahmadian et al.

(10) Patent No.: US 9,983,147 B2
(45) Date of Patent: May 29, 2018

(54) SYSTEM AND METHOD FOR PROGNOSTIC HEALTH MONITORING OF THERMAL BARRIER COATINGS

(71) Applicant: UNITED TECHNOLOGIES CORPORATION, Hartford, CT (US)

(72) Inventors: Shayan Ahmadian, Vernon, CT (US); Thomas J. Martin, East Hampton, CT (US); Alexander Staroselsky, Avon, CT (US); Charles W. Haldeman, Simsbury, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 0 days. days.

(21) Appl. No.: 15/057,962

(22) Filed: Mar. 1, 2016

(65) Prior Publication Data

US 2017/0254761 A1    Sep. 7, 2017

(51) Int. Cl.
*G01N 21/00* (2006.01)
*G01N 21/94* (2006.01)
*G01M 15/14* (2006.01)
*G01N 21/954* (2006.01)
*G01N 25/72* (2006.01)
(Continued)

(52) U.S. Cl.
CPC ............ *G01N 21/94* (2013.01); *G01J 5/0022* (2013.01); *G01M 15/14* (2013.01); *G01N 21/954* (2013.01); *G01N 25/72* (2013.01); *G05B 23/024* (2013.01)

(58) Field of Classification Search
CPC ...... G01M 15/14; G01N 21/954; G01N 21/94

USPC .............. 356/237.1–237.6, 236.1–239.8
See application file for complete search history.

(56) References Cited

U.S. PATENT DOCUMENTS

| 7,690,840 B2 * | 4/2010 | Zombo ............... F01D 5/288 |
| | | 250/338.1 |
| 2003/0115941 A1 * | 6/2003 | Srivastava ......... G01N 21/6489 |
| | | 73/114.79 |

(Continued)

FOREIGN PATENT DOCUMENTS

WO         0146660         6/2001

OTHER PUBLICATIONS

J. A. Nychka, T. Naganuma, M. R. Winter, Y. Kagawa, and D. R. Clarke,"Temperature Dependent Optical Reflectivity of Tetragonal-Prime Yttria stabilized Zirconia," J. Am. Ceram. Soc., 89 908-913 (2006).

(Continued)

*Primary Examiner* — Tri T Ton
(74) *Attorney, Agent, or Firm* — Snell & Wilmer, L.L.P.

(57) ABSTRACT

A system and method for prognostic health monitoring of thermal barrier coatings is provided. The system may comprise monitoring a thermal barrier coated gas turbine engine component, and measuring the infrared radiation emitting from the component. The measured thermal radiation data may be analyzed and compared to known material thermal radiation data in order to determine the health of the thermal barrier coating. The compiled comparison results may be compared against a historical statistical study to then determine the overall health of the thermal barrier coating. The system may comprise generating a health monitoring alert in response to the health of the thermal barrier coating indicating an imminent failure.

20 Claims, 4 Drawing Sheets

(51) Int. Cl.
    G05B 23/02    (2006.01)
    G01J 5/00     (2006.01)

(56) References Cited

U.S. PATENT DOCUMENTS

2003/0127602 A1* 7/2003 Harrold .................. G01J 1/429
                                                        250/372
2005/0023468 A1* 2/2005 Saito ...................... G01N 25/72
                                                        250/341.6

OTHER PUBLICATIONS

J. I. Eldridge, C. M. Spuckler, K. W. Street, and J. R. Markham, "Infrared Radiative Properties of Yttria—Stabilized Zirconia Thermal Barrier Coatings", Proc. Ceramic Sci. Eng., 23 [4] 417-430 (2002).

P. D. LeVan and D. Maestas, A., "3.5 to 12 micron dual-band spectrometer", Opt. Eng. 43 (12), pp. 3045-3054, 2004.

Estevadeordal, J., Wang, G., Nirmalan, N., Wang, A., Harper, S. P., and Rigney, J. D., "Multicolor Techniques for Identification and Filtering of Burst Signals in Jet Engine Pyrometers", J. of Turbomachinery, ASME, vol. 136, Mar. 2014.

J.I. Eldrich et al, "Determination of scattering and absorption coefficients for plasma sprayed yttria stablized zirconia thermal barrier coating at elevated temperatures".

EP Search report dated Jun. 29, 2017 in EP Application No. 17158527.6.

* cited by examiner

SYSTEM AND METHOD FOR PROGNOSTIC HEALTH MONITORING OF THERMAL BARRIER COATINGS

FIELD

The present disclosure relates to thermal barrier coatings in gas turbine engines, and more specifically, to a method for monitoring the health of thermal barrier coatings.

BACKGROUND

Hot section turbine components in aircraft and industrial gas turbine engines may be protected by thermal barrier coatings ("TBCs") that provide thermal insulation against high temperatures. TBCs may be used to protect metallic parts, such as, turbine blades, vanes, endwalls, air seals, and/or combustor lines. During engine operation, TBCs may be prone to rapid degeneration in service due to high temperatures and oxidizing environments, and thermal cycling. TBCs may delaminate and experience spalling during continuous operation. The rate of TBC loss may be made significantly worse due to high-temperature thermal cycling. As TBCs delaminate and spall, bare metal alloy may be exposed to high-temperature combustion product gasses, which may rapidly deteriorate the metal and/or alloy substrate. The rapid deterioration may result in vastly shortened operating life-times, among other issues.

SUMMARY

In various embodiments, a system for prognostic health monitoring of thermal barrier coatings is disclosed. The system may comprise an optical sensor configured to monitor a thermal barrier coating (TBC) coated turbine component. The system may comprise a processor configured to perform operations. The processor may calculate a measured thermal radiation data from the TBC coated turbine component. The processor may retrieve a known material thermal radiation data. The processor may compare the measured thermal radiation data to the known material thermal radiation data to detect the presence of a foreign particle on the TBC coated turbine component, and to detect a degradation of the TBC coated turbine component. The processor may compile the comparison results of the measured thermal radiation data to the known material thermal radiation data to determine an overall health of the TBC coated turbine component.

In various embodiments the system may compare the compiled comparison results to a historical study to determine a useful life of the TBC coated turbine component. The useful life may comprise a percentage indicating an amount of the useful life remaining in the TBC coated turbine component.

In various embodiments, the system may generate a health monitoring alert when the TBC coated turbine component is below 20% of the useful life. In various embodiments, the system may transmit the health monitoring alert to a fleet monitoring system for maintenance of the TBC coated turbine component.

In various embodiments, the known material thermal radiation data may comprise a known measured thermal radiation properties of a soil, a soot, and/or a sand constituent. In various embodiments, the known material thermal radiation data may comprise a known measured thermal radiation properties of a TBC coating on the TBC coated turbine component, a metal alloy of the TBC coated turbine component, a 80% degenerated TBC coated turbine component, a 60% degenerated TBC coated turbine component, a 40% degenerated TBC coated turbine component, and/a 20% degenerated TBC coated turbine component. In various embodiments, the known material thermal radiation data may be stored in a library of known material thermal radiation properties.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the following illustrative figures. In the following figures, like reference numbers refer to similar elements and steps throughout the figures.

Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the disclosures, it should be understood that other embodiments may be realized and that logical changes and adaptations in design and construction may be made in accordance with this disclosure and the teachings herein. Thus, the detailed description herein is presented for purposes of illustration only and not of limitation.

The scope of the disclosure is defined by the appended claims and their legal equivalents rather than by merely the examples described. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, coupled, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts but not necessarily to denote the same or different materials.

Figure 1:
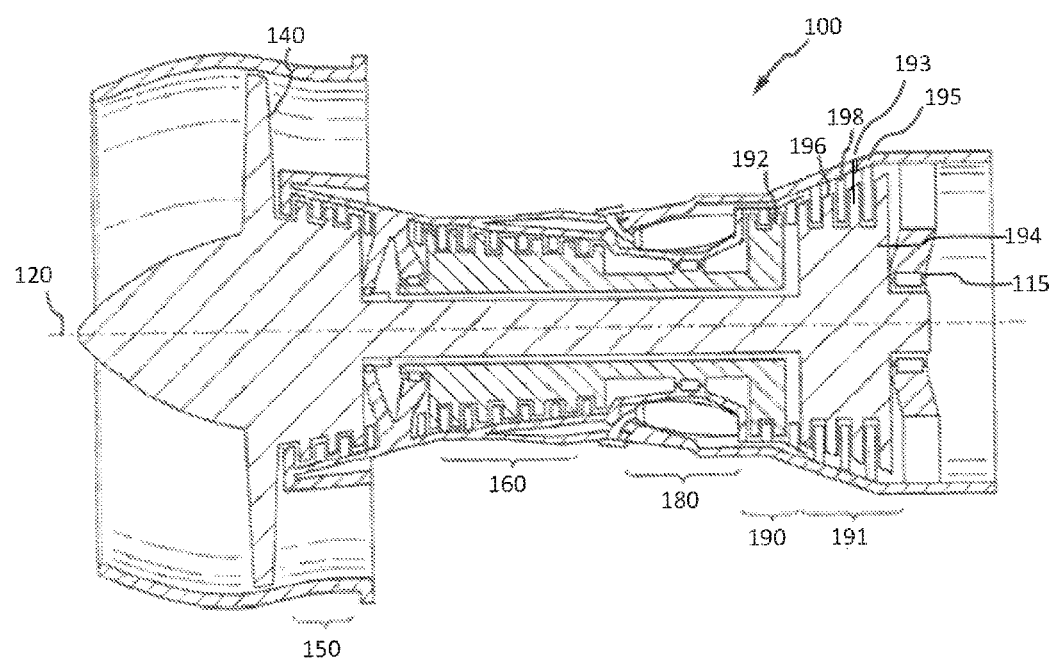
FIG. 1 illustrates a gas turbine engine, in accordance with various embodiments.

In various embodiments, and with reference to FIG. 1, a gas turbine engine 100 (such as a turbofan gas turbine engine) is illustrated. Gas turbine engine 100 is disposed about axial centerline axis 120, which may also be referred to as axis of rotation 120. Gas turbine engine 100 may comprise a fan 140, compressor sections 150 and 160, a combustion section 180, and turbine sections 190, 191. The fan 140 may drive air into compressor sections 150, 160, which may further drive air along a core flow path for compression and communication into the combustion section 180. Air compressed in the compressor sections 150, 160 may be mixed with fuel and burned in combustion section 180 and expanded across the turbine sections 190, 191. The turbine sections 190, 191 may include high pressure rotors 192 and low pressure rotors 194, which rotate in response to the expansion. The turbine sections 190, 191 may comprise alternating rows of rotary airfoils or blades 196 and static airfoils or vanes 198, housed within an engine casing 195. Cooling air may be supplied to the turbine sections 190, 191 from the compressor sections 150, 160. A plurality of bearings 115 may support spools in the gas turbine engine 100. FIG. 1 provides a general understanding of the sections in a gas turbine engine, and is not intended to limit the disclosure. The present disclosure may extend to all types of applications and to all types of turbine engines, including turbofan gas turbine engines and turbojet engines.

In various embodiments, gas turbine engine 100 components in turbine sections 190, 191 may be subject to very high temperatures during operation, often twice as high as the melting point of the metal component itself. The gas turbine engine 100 components may be protected from the high temperatures by a TBC and/or by an environmental barrier coating ("EBC"). The TBC may provide thermal insulation to the turbine components, and the EBC may provide resistance to oxidation and/or corrosion. The TBC may comprise a ceramic-based material. For example, the TBC may comprise at least 5% yttria partially-stabilized zirconia (e.g., 7YPSZ, 7% yttria, Y203 with respect to zirconia). The TBC may be used to coat various turbine components, such as rotary airfoils or blades 196 and/or static airfoils or vanes 198. The TBC may also be used to coat any other suitable component, such as a blade outer air seal, combustor liners, and/or other surfaces of turbine sections 190, 191. The TBC may allow higher gas temperature operation by protecting parts exposed to high-temperature gases from thermally activated damage such as melting, creep, oxidation, corrosion, and cyclic thermal-mechanical fatigue. This protection may result in improved fuel consumption, increased thrust or power generation, reduced emissions, improved reliability, reduced cooling requirements, and reduced cost by extending the service life and time between maintenance intervals of the components.

The TBC may be prone to rapid degeneration during operation of gas turbine engine 100. The TBC may delaminate, erode, oxidize, and/or spall off during continuous engine operation, and the rate of the TBC degeneration may be made significantly worse due to high-temperature thermal cycling. Moreover, the TBC may be covered with dirt, sand, and/or other such similar objects that may flow through gas turbine engine 100 during operation, causing damage to the TBC layer. After a period of time under these conditions, the TBCs may begin to fail, exposing the bare metal alloy of the coated turbine components to high-temperature combustion product gases. Under these conditions, the bare metal alloy surface of the turbine components may rapidly deteriorate, resulting in vastly shortened operating times.

Principles from the current disclosure may be used to monitor the health of a TBC coated turbine components. In various embodiments, the system may monitor the health of the TBC coated turbine components in real-time, and while gas turbine engine 100 is in operation. The system may determine the health of the TBC coated turbine components by determining the amount of contaminant accumulated on TBC coated surfaces, and by determining the damage progression of the TBC coated surfaces. Using those two determinations, the system may calculate the overall health of the TBC coated turbine components, and determine how close the component is to ultimate part failure. In various embodiments, and with reference to FIG. 2A, system 200 may be configured to monitor the health of the TBC coated turbine components. System 200 may comprise a processor 210, an optical sensor 220, a TBC coated turbine component 230, a prognostics and health management ("PHM") database 240, and a library of known material thermal radiation properties 250.

In various embodiments, processor 210 may comprise any suitable processor capable of receiving data and performing operations. Processor 210 may be configured to perform the calculations associated with monitoring the health of TBC coated turbine component 230. Processor 210 may be located onboard an aircraft, and/or located externally from an aircraft. In this regard, processor 210 may be located within the aircraft's full authority digital engine control ("FADEC"), and/or located within the aircraft's health monitoring systems. Processor 210 may also be located off-board the aircraft, in any suitable computer-based system. Processor 210 may also be configured to execute instructions loaded onto a tangible, non-transitory computer readable medium, causing processor 210 to perform various operations. Processor 210 may be in logical and/or electronic communication with optical sensor 220, PHM database 240, and/or library of known material thermal radiation properties 250. Processor 210 may be in logical and/or electronic communication using any method disclosed herein or known in the art.

In various embodiments, optical sensor 220 may be configured to monitor TBC coated turbine component 230. Optical sensor 220 may be configured to monitor TBC coated turbine component 230, and record the measured IR spectrum properties emitted from TBC coated turbine component 230. Optical sensor 220 may record the measured IR spectrum properties as a measured thermal radiation data. Optical sensor 220 may be in logical and/or electronic communication with processor 210 and PHM database 240. Optical sensor 220 may be in logical and/or electronic communication using any method disclosed herein or known in the art. Optical sensor 220 may record the measured thermal radiation data and transmit the measured thermal radiation data to PHM database 240 for storage. In various embodiments, optical sensor 220 may also transmit the measured thermal radiation data directly to processor 210.

In various embodiments, the measured thermal radiation data may comprise data and measured properties of TBC coated turbine component 230. The measured thermal radiation data may comprise data on the spectrum (intensity as a function of wavelength) of TBC coated turbine component 230. For example, the measured thermal radiation data may comprise data regarding the measured emissivity, absorptivity, reflectivity, and transmissivity of the thermal radiation of TBC coated turbine component 230. As such, the measured thermal radiation data may comprise any data related to the measured thermal radiation of TBC coated turbine component 230.

In various embodiments, optical sensor 220 may be located in any location suitable for monitoring TBC coated turbine component 230. For example, optical sensor 220 may be located in the gas turbine engine, in a location proximate to TBC coated turbine component 230. In this regard, and with reference again to FIG. 1, optical sensor 220 may be inserted through a hole 193 located in engine casing 195, in a proximal location to TBC coated turbine component 230. Hole 193 may comprise a borescope port preexisting in engine casing 195. For example, if TBC coated turbine component 230 comprises rotary airfoils or blades 196 or static airfoils or vanes 198, hole 193 may be located in engine casing 195 nearest to that particular TBC coated turbine component 230. Monitoring TBC coated turbine component 230 through this method may be accomplished through the use of a flexible borescope. The flexible borescope may be inserted through hole 193 in engine casing 195, and used to monitor TBC coated turbine component 230.

In various embodiments, optical sensor 220 may comprise any suitable apparatus capable of monitoring the IR spectrum emitted from TBC coated turbine component 230. Optical sensor 220 may comprise any suitable apparatus capable of acquiring and/or sensing radiation over any suitable spectral range. In this regard, optical sensor 220 may monitor radiation over a spectral range of 0.5 µm to about 1000 µm in wavelength. For example, optical sensor 220 may acquire and/or sense radiation over a near-IR spectral range of 0.5 µm to about 5 µm, a mid-IR spectral range of about 5 µm to about 25 µm, and/or a long-IR spectral range of about 25 µm to about 1000 µm. In various embodiments, optical sensor 220 may be configured to acquire and/or sense radiation over a spectral range of 0.5 µm to 14.5 µm in wavelength.

In various embodiments, optical sensor 220 may comprise an IR camera, such as, for example, a short-wave IR camera, mid-wave IR camera, or long-wave IR camera. Optical sensor 220 may comprise a Fourier transform infrared ("FTIR") spectroscope, IR spectrometer, spectral pyrometer, emissometer, and/or the like. Optical sensor 220 may comprise a spectrometer having two or more focal plane arrays ("FPAs") wherein the optical image is transmitted through a beam splitter, such as a grating or prism. For example, and with reference to FIG. 2B, a dual-channel spectrometer 225 of the prior art is disclosed. Dual-channel spectrometer 225 may comprise a first focal plane array 226, a second focal plane array 227, and a beamspliter 228. Optical sensor 220 may also comprise a more complicated spectrometer comprising more than two FPAs.

In various embodiments, TBC coated turbine component 230 may comprise the TBC coated components of the gas turbine engine that are being monitored for health. In this regard, TBC coated turbine component 230 may comprise any TBC coated component in a gas turbine engine that is suitable to be monitored for health. TBC coated component 230 may comprise the alternating rows of rotary airfoils or blades 196, the static airfoils or vanes 198, or any of the other components in FIG. 1. For example, TBC coated turbine component 230 may comprise metallic components in the hot section of gas turbine engines, such as, for example, turbine blades, vanes, endwalls, air seals, combustor liners, and/or the like.

In various embodiments, PHM database 240 may be configured to receive and store the measured thermal radiation data. PHM database 240 may store the measured thermal radiation data using any suitable method disclosed herein or known in the art. PHM database 240 may be in logical and/or electronic communication with processor 210 and optical sensor 220. PHM database 240 may be in logical and/or electronic communication using any method disclosed herein or known in the art.

In various embodiments, library of known material thermal radiation properties 250 may be configured to store a known material thermal radiation data. Library of known material thermal radiation properties 250 may comprise any suitable method for storing the known material thermal radiation data, such as through the use of a database. Library of known material thermal radiation properties 250 may store the known material thermal radiation data using any suitable method disclosed herein or known in the art. Library of known material thermal radiation properties 250 may be in logical and/or electronic communication with processor 210. Library of known material thermal radiation properties 250 may be in logical and/or electronic communication using any method disclosed herein or known in the art.

In various embodiments, the known material thermal radiation data may comprise data relating to the measured thermal emittance of TBC coated turbine component 230 and materials known to affect TBC surface coatings. Data relating to the measured thermal emittance may include data on the spectrum (intensity as a function of wavelength) of the materials, such as known emissivity, absorptivity, reflectivity, and transmissivity measurements. The known material thermal radiation data may comprise both data relating to TBC coated turbine component 230 and/or data relating to foreign particles that may gather on TBC coated turbine component 230.

In various embodiments, data relating to TBC coated turbine component 230 may comprise the known measured thermal radiation properties of the TBC coating. For example, in the near IR and shortwave IR spectrums, the TBC coating may be mostly translucent, and may comprise thermal radiation properties of about 5% absorptance, about 20% reflectance, and about 75% transmittance. Data relating to TBC coated turbine component 230 may also comprise the known measured thermal radiation properties of the TBC coating in various stages of deterioration (e.g., from 0% to 20%, 40%, 60%, 80%, etc. deterioration), the known measured thermal radiation properties of the underlying metal alloy of the turbine component (e.g., TBC coated turbine component 230 with the TBC coating 100% deteriorated), and/or the like. The known measured thermal radiation properties of the TBC coating may change in a known and predictable way as the TBC coating deteriorates. For example, as the TBC coating begins to deteriorate, the transmittance may continue to increase from 75% until the TBC coating spalls and reaches 100% transmittance.

In various embodiments, data relating to foreign particles may comprise the known measured thermal radiation properties of various materials, such as temperature, emissivity v. temperature, reflectivity v. temperature, and/or transmissivity. The properties may be integrated over all wavelengths. For example, for a nickel-based superalloy, library of known material thermal radiation properties 250 may store a temperature range of 100° C. (212° F.) to 1300° C. (2372° F.), an emissivity v. temperature range of 0.87 to 0.89, a reflectivity v. temperature range of 0.13 to 0.11, and a transmissivity of 0%. For example, for a nickel-chromium alloy (such as that sold under the mark INCONEL, e.g., INC- ONEL 600, 617, 625, 718, X-70, and the like), a temperature range of 450° C. (450° F.) to 1620° C. (2948° F.), an emissivity v. temperature range of 0.35 to 0.55, and a reflectivity v. temperature range of 0.65 to 0.45 may be stored. For example, for a silica material, a temperature range of 1010° C. (1850° F.) to 1566° C. (2850.8° F.), and an emissivity v. temperature range of 0.62 to 0.46 may be stored. For example, for a soot, a temperature range of 50° C. (112° F.) to 1000° C. (1832° F.), an emissivity v. temperature of 0.96, a reflectivity v. temperature range of 0.04, and a transmissivity of 0% may be stored. For example, for a chromia material, a temperature range of 100° C. (212° F.) to 982° C. (1799.6° F.), and an emissivity v. temperature range of 0.08 to 0.66 may be stored. For example, for an alumina material, a temperature range of 500° C. (932° F.) to 827° C. (1520.6° F.), and an emissivity v. temperature range of 0.26 to 0.42 may be stored. For example, for an iron oxide material, a temperature range of 500° C. (932° F.) to 1200° C. (2192° F.), and an emissivity v. temperature range of 0.85 to 0.89 may be stored. For example, for a nickel oxide material, a temperature range of 650° C. (1202° F.) to 1254° C. (2289.2° F.), and an emissivity v. temperature range of 0.59 to 0.86 may be stored. For example, for a magnesium oxide material, a temperature range of 227° C. (440.6° F.) to 1704° C. (3099.2° F.), and an emissivity v. temperature range of 0.55 to 0.2 may be stored. The above referenced values are for example purposes only, and the materials referenced may comprise other valid values and ranges that may be stored. Similarly, other materials, and values and ranges for those materials, may also be stored.

Figure 2A:
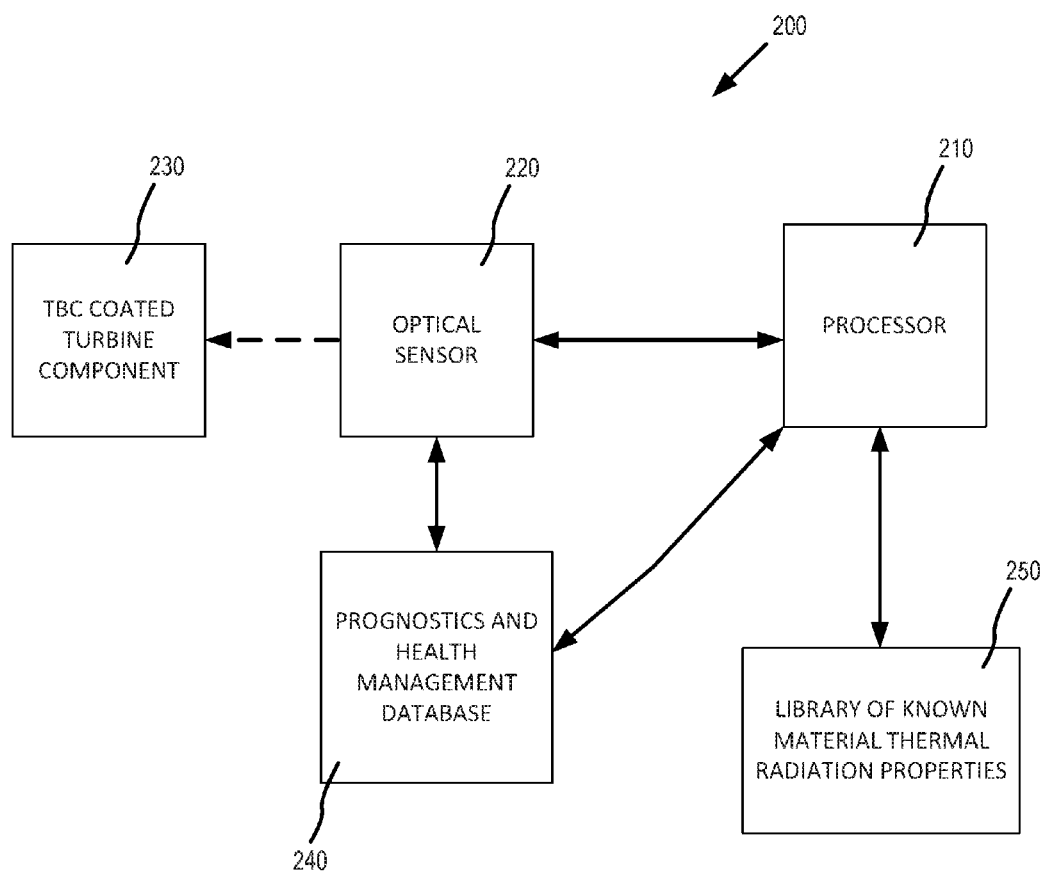
FIG. 2A illustrates a block diagram for a system for prognostic health monitoring of thermal barrier coatings, in accordance with various embodiments.
Figure 2B:
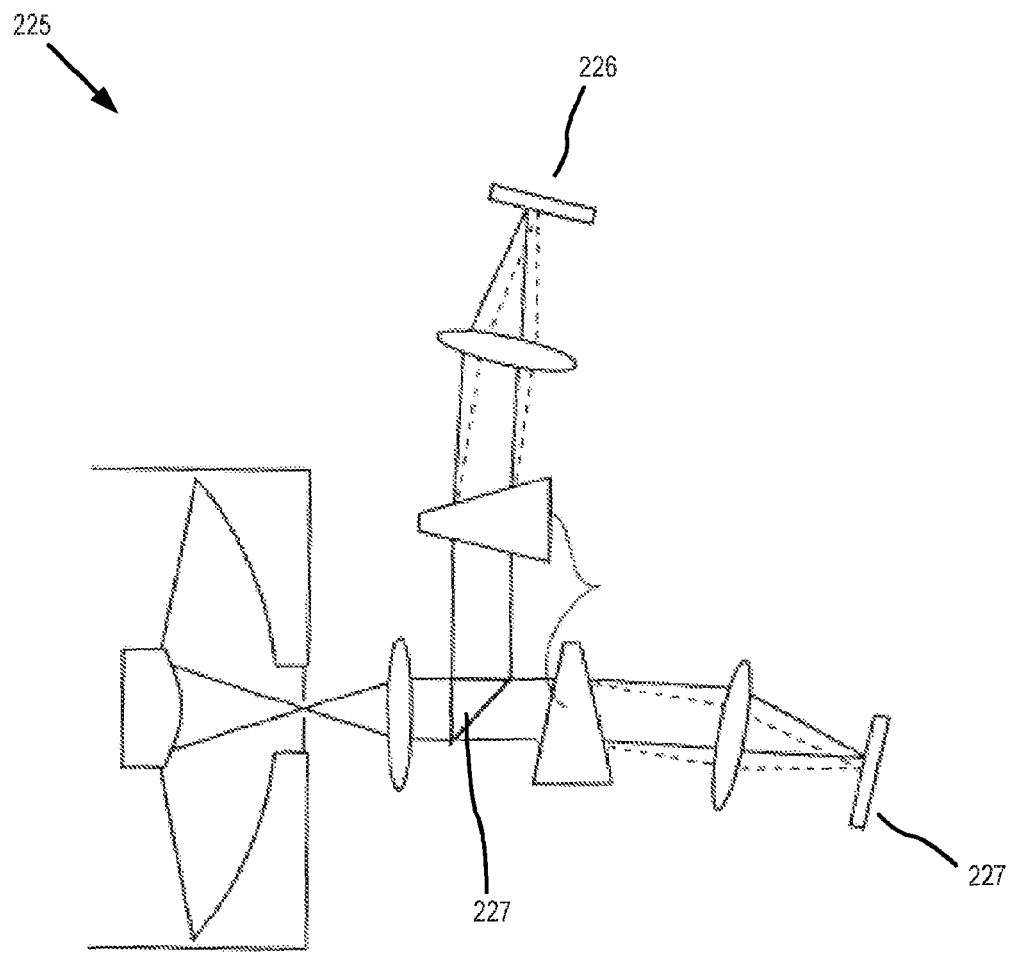
FIG. 2B illustrates a spectrometer for a method for prognostic health monitoring of thermal barrier coatings, in accordance with various embodiments.
Figure 3:
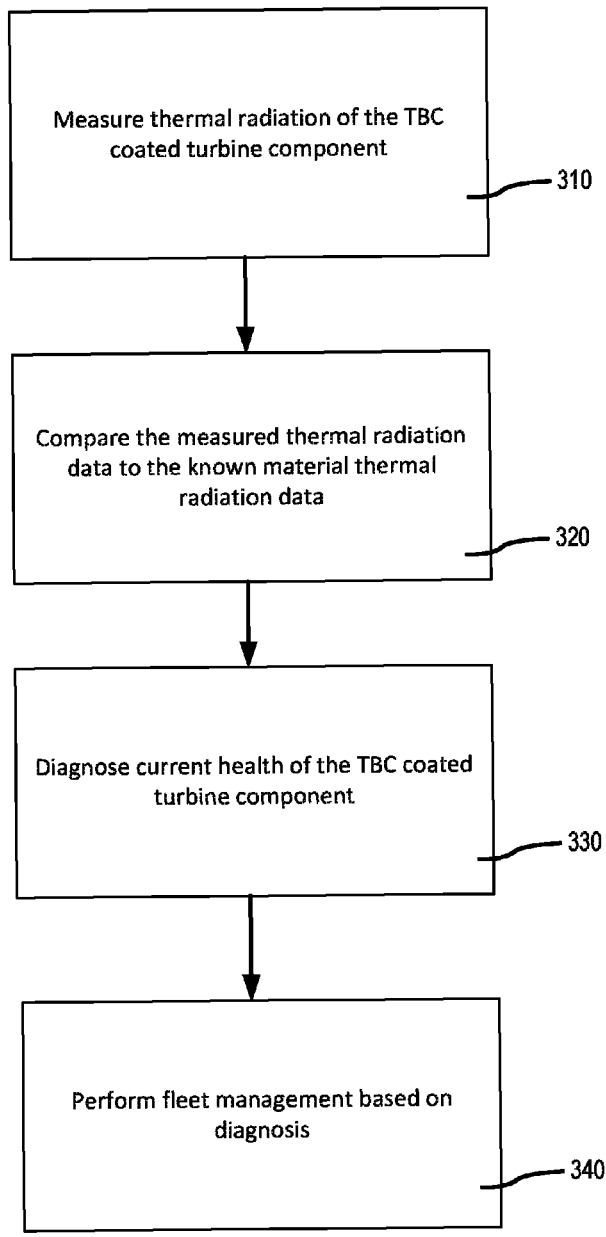
FIG. 3 illustrates a process flow for prognostic health monitoring of thermal barrier coatings, in accordance with various embodiments.

In various embodiments, with reference to FIG. 3 and further reference to FIG. 2A, a method 300 for the health monitoring of TBCs is disclosed. Method 300 may comprise measuring thermal radiation of the TBC coated turbine component 230 to determine the measured thermal radiation data of TBC coated turbine component 230 (step 310). The thermal radiation of TBC coated turbine component 230 may be measured by optical sensor 220. Processor 210 may be configured to operatively instruct optical sensor 220 to measure the thermal radiation of TBC coated turbine component 230. Optical sensor 220 may be configured to measure the thermal radiation by taking a bandwidth of IR intensities from TBC coated turbine component 230 in any suitable range. For example, optical sensor 220 may take a bandwidth of IR intensities with the IR spectrum of 2-20 microns. Optical sensor 220 may be configured to take several measurements for each of the measured thermal radiation data. Optical sensor 220 may take any suitable number of measurements to fully ensure accurate IR intensity measurements, such as, for example, three, four, or one hundred measurements. A high number of thermal radiation measurements may enable a greater accuracy in the measured thermal radiation data. Optical sensor 220 may monitor and measure the thermal radiation of the entire TBC coated turbine component 230 one surface area at a time, such that optical sensor 220 may capture data on the entire surface area of TBC coated turbine component 230.

In various embodiments, as optical sensor 220 measures the thermal radiation of TBC coated turbine component 230, optical sensor 220 may also be configured to transmit the measured thermal radiation data for analysis. Optical sensor 220 may transmit the measured thermal radiation data to PHM database 240 for storage. In various embodiments, optical sensor 220 may also be configured to transmit the measured thermal radiation data directly to processor 210 for analysis.

In various embodiments, method 300 may comprise comparing the measured thermal radiation data to the known material thermal radiation data (step 320). Processor 210 may retrieve the measured thermal radiation data from PHM database 240. Processor 210 may also be configured to directly receive the measured thermal radiation data from optical sensor 220. Processor 210 may communicate with library of known material thermal radiation properties 250 to access and retrieve the known material thermal radiation data.

In various embodiments, processor 210 may compare the measured thermal radiation data to the known material thermal radiation data by checking whether the thermal radiation of the measured thermal radiation data matches the known material thermal radiation data. In this regard, a match of the thermal of the measured thermal radiation data to the thermal radiation of the known material thermal radiation data will inform on the health of TBC coated turbine component 230. For example, a match of the measured thermal radiation data to the known material thermal radiation data comprising a dirt constituent, such as soot, would indicate a deposit on TBC coated turbine component 230 in the measured surface area. As a further example, a match of the measured thermal radiation data to the known material thermal radiation data comprising a thermal radiation measurement indicating a degeneration of TBC (such as a TBC degenerated by spalling and/or sintering), would indicate a degeneration to the health of the TBC coating in the measured surface area of TBC coated turbine component 230. If the thermal radiation of the measured thermal radiation data does not match with a thermal radiation of the known material thermal radiation data, then that measured area of the monitored TBC coated turbine component 230 has no degeneration and no surface area defect.

In various embodiments, method 300 may comprise diagnosing the current health of TBC coated turbine component 230 (step 330). Processor 210 may analyze the results of the comparisons of the measured thermal radiation data to the known material thermal radiation data to create a compiled comparison results. By combining all of the comparisons of the measured thermal radiation data of TBC coated turbine component 230 to the known material thermal radiation data in library of known material thermal radiation properties 250, the health of the TBC coating surface area of TBC coated turbine component 230 may be mapped out. In this regard, the compiled comparison results will provide the overall health of TBC coated turbine component 230 by indicating the health of each individual measurement.

In various embodiments, processor 210 may be configured to display the compiled comparison results. In this regard, processor 210 may be configured to transmit the compiled comparison results to a visual display device, such as a computer monitor and/or the like. Processor 210 may also be configured to transmit a message along with the compiled comparison results, explaining the comparison of the measured thermal radiation data of TBC coated turbine component 230 to the known material thermal radiation data. Processor 210 may also be configured to transmit the compiled comparison results for further analysis, such as, for example, by a separate system or module.

In various embodiments, the compiled comparison results may be compared against a historical statistical study to diagnose the current health of TBC coated turbine component 230. For example, the historical statistical study may comprise similar TBC coated turbine components 230 in varying stages of degeneration (such as 30%, 50%, 90% degraded, and/or the like). The historical statistical study may be compared with the compiled comparison results to provide an understanding of the overall health of TBC coated turbine components 230. For example, in response to the compiled comparison results matching the historical statistical study comprising a 30% degradation, TBC coated turbine component 230 may have a current health of 70%.

In various embodiments, method 300 may comprise performing fleet management based on the current health of TBC coated turbine component 230 (step 340). Here, in response to the results of the comparison of the compiled comparison results and the historical statistical study, processor 210 may be configured to generate a health monitoring alert. In various embodiments where processor 210 comprises a processor on-board an aircraft, the health monitoring alert may be used in real-time to alert a possible failure of TBC coated turbine component 230, or alert that TBC coated turbine component 230 is in a health condition that could cause an imminent failure. The health monitoring alert may also be used to adjust an engine control computer to increase, maximize, or improve the life durability of the engine. For example, in response to receiving the health monitoring alert related to TBC coated turbine component 230, the engine control computer may adjust the speed, the gas temperature, and the amount of fuel that is fed to the engine to maintain flight speed, in order to avoid rapid increases and decreases in temperature that may further damage TBC coated turbine component 230.

In various embodiments where processor 210 comprises a processor off-board an aircraft, the health monitoring alert may be used as a fleet management and maintenance tool. The health monitoring alert may be transmitted to a fleet management system for fleet management and maintenance of the aircraft. For example, instead of interval based maintenance for aircraft fleets, the health monitoring alert may be used to enable maintenance of only TBC coated turbine component 230 that are in poor health. In this regard, wasted maintenance times may tend to be minimized, as only TBC coated turbine component 230 that need maintenance, will undergo maintenance.

Computer-based system program instructions and/or processor instructions may be loaded onto a tangible, non-transitory computer readable medium having instructions stored thereon that, in response to execution by a processor, cause the processor to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

As used herein, "match" or "associated with" or similar phrases may include an identical match, a partial match, meeting certain criteria, matching a subset of data, a correlation, satisfying certain criteria, a correspondence, an association, an algorithmic relationship and/or the like. As used herein, "transmit" may include sending electronic data from one system component to another over a network connection. Additionally, as used herein, "data" may include encompassing information such as commands, queries, files, data for storage, and the like in digital or any other form.

Any databases discussed herein may include relational, hierarchical, graphical, or object-oriented structure and/or any other database configurations. Common database products that may be used to implement the databases include DB2 by IBM® (Armonk, N.Y.), various database products available from ORACLE® Corporation (Redwood Shores, Calif.), MICROSOFT® Access® or MICROSOFT® SQL Server® by MICROSOFT® Corporation (Redmond, Wash.), MySQL by MySQL AB (Uppsala, Sweden), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosures. The scope of the disclosures is accordingly to be limited by nothing other than the appended claims and their legal equivalents, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and computer program products are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system, comprising:
   an optical sensor configured to monitor a thermal barrier coating (TBC) coated turbine component installed in a gas turbine engine in real time during operation of the gas turbine engine; and
   a processor, wherein the processor is configured to perform operations comprising:
   calculating, by the processor, a measured thermal radiation data from the TBC coated turbine component, wherein the measured thermal radiation data comprises at least one of measured emissivity, absorptivity, reflectivity, or transmissivity of a thermal radiation of the TBC coated turbine component and wherein the thermal radiation is emitted from the TBC coated turbine component while the gas turbine engine is operating;
   retrieving, by the processor, a known material thermal radiation data;
   comparing, by the processor, the measured thermal radiation data to the known material thermal radiation data to detect a presence of a foreign particle on the TBC coated turbine component and to detect a degradation of the TBC coated turbine component; and
   compiling, by the processor, the comparison results of the measured thermal radiation data to the known material thermal radiation data to determine an overall health of the TBC coated turbine component.

2. The system of claim 1, wherein the operations further comprise comparing the compiled comparison results to a historical statistical study to determine a useful life of the TBC coated turbine component, wherein the useful life comprises a percentage indicating an amount of the useful life remaining in the TBC coated turbine component.

3. The system of claim 2, wherein the operations further comprise generating a health monitoring alert when the TBC coated turbine component is below 20% of the useful life.

4. The system of claim 3 wherein the operations further comprise transmitting the health monitoring alert to a fleet monitoring system for maintenance of the TBC coated turbine component.

5. The system of claim 1, wherein the known material thermal radiation data comprises at least one of a known measured thermal radiation properties of a soil, a soot, and a sand constituent.

6. The system of claim 1, wherein the known material thermal radiation data comprises at least one of a known measured thermal radiation properties of a TBC coating on the TBC coated turbine component, a metal alloy of the TBC coated turbine component, a 80% degenerated TBC coated turbine component, a 60% degenerated TBC coated turbine component, a 40% degenerated TBC coated turbine component, and a 20% degenerated TBC coated turbine component.

7. The system of claim 1, wherein the known material thermal radiation data is stored in a library of known material thermal radiation properties.

8. A method, comprising:
   calculating, by a processor and via an optical sensor, a measured thermal radiation data from a TBC coated turbine component installed in a gas turbine engine, wherein the measured thermal radiation data comprises at least one of measured emissivity, absorptivity, reflectivity, or transmissivity of a thermal radiation of the TBC coated turbine component and wherein the thermal radiation is emitted from the TBC coated turbine component while the gas turbine engine is operating;
   retrieving, by the processor, a known material thermal radiation data;
   comparing, by the processor, the measured thermal radiation data to the known material thermal radiation data to detect a presence of a foreign particle on the TBC coated turbine component and to detect a degradation of the TBC coated turbine component; and
   compiling, by the processor, the comparison results of the measured thermal radiation data to the known material thermal radiation data to determine an overall health of the TBC coated turbine component;
   wherein the calculating, retrieving, comparing, and compiling are performed in real time while the gas turbine engine is in operation.

9. The method of claim 8, wherein the processor is further configured to compare the compiled comparison results to a historical statistical study to determine a useful life of the TBC coated turbine component, wherein the useful life comprises a percentage indicating an amount of useful life remaining in the TBC coated turbine component.

10. The method of claim 9, wherein the processor is further configured to generate a health monitoring alert when the TBC coated turbine component is below 20% of the useful life.

11. The method of claim 10, wherein the processor is further configured to transmit the health monitoring alert to a fleet monitoring system for maintenance of the TBC coated turbine component.

12. The method of claim 8, wherein the known material thermal radiation data comprises at least one of the known measured thermal radiation properties of a soil, a soot, and a sand constituent.

13. The method of claim 8, wherein the known material thermal radiation data comprises at least one of a known measured thermal radiation properties of a TBC coating on the TBC coated turbine component, a metal alloy of the TBC coated turbine component, a 80% degenerated TBC coated turbine component, a 60% degenerated TBC coated turbine component, a 40% degenerated TBC coated turbine component, and a 20% degenerated TBC coated turbine component.

14. The method of claim 8, wherein the known material thermal radiation data is stored in a library of known material thermal radiation properties.

15. An article of manufacture including a tangible, non-transitory computer-readable storage medium having instructions stored thereon that, in response to execution by a processor, cause the processor to perform operations comprising:

calculating, by a processor and via an optical sensor, a measured thermal radiation data from a TBC coated turbine component installed in a gas turbine engine, wherein the measured thermal radiation data comprises at least one of measured emissivity, absorptivity, reflectivity, or transmissivity of a thermal radiation of the TBC coated turbine component and wherein the thermal radiation is emitted from the TBC coated turbine component while the gas turbine engine is operating;

retrieving, by the processor and via a library of known material thermal radiation properties, a known material thermal radiation data;

comparing, by the processor, the measured thermal radiation data to the known material thermal radiation data to detect a presence of a foreign particle on the TBC coated turbine component and to detect a degradation of the TBC coated turbine component; and compiling, by the processor, the comparison results of the measured thermal radiation data to the known material thermal radiation data to determine an overall health of the TBC coated turbine component;

wherein the calculating, retrieving, comparing, and compiling are performed in real time while the gas turbine engine is in operation.

16. The article of manufacture of claim 15, wherein operations further comprise comparing, by the processor, the compiled comparison results to a historical statistical study to determine a useful life of the TBC coated turbine component, wherein the useful life comprises a percentage indicating an amount of useful life remaining in the TBC coated turbine component.

17. The article of manufacture of claim 16, wherein operations further comprise generating, by the processor, a health monitoring alert when the TBC coated turbine component is below 20% of the useful life.

18. The article of manufacture of claim 17, wherein operations further comprise transmitting, by the processor, the health monitoring alert to a fleet monitoring system for maintenance of the TBC coated turbine component.

19. The article of manufacture of claim 15, wherein the known material thermal radiation data comprises at least one of the known measured thermal radiation properties of a soil, a soot, and a sand constituent.

20. The article of manufacture of claim 15, wherein the known material thermal radiation data comprises at least one of a known measured thermal radiation properties of a TBC coating on the TBC coated turbine component, a metal alloy of the TBC coated turbine component, a 80% degenerated TBC coated turbine component, a 60% degenerated TBC coated turbine component, a 40% degenerated TBC coated turbine component, and a 20% degenerated TBC coated turbine component.

* * * * *